United States Patent [19]

Springer et al.

[11] Patent Number: 5,462,855
[45] Date of Patent: Oct. 31, 1995

[54] METHOD FOR THE DETECTION AND QUANTITATIVE DETERMINATION OF NITROSOMONAS STRAINS IN WASTEWATERS OR SOILS

[75] Inventors: Wolfgang Springer, Wuppertal; Hans G. Rast, Bergisch Gladbach; Antonius Löbberding, Wuppertal; Reinhard Kanne, Leverkusen, all of Germany

[73] Assignee: Bayer Aktiengesellschaft, Leverkusen, Germany

[21] Appl. No.: 55,945

[22] Filed: Apr. 30, 1993

Related U.S. Application Data

[63] Continuation of Ser. No. 692,745, Apr. 24, 1991, abandoned.

[30] Foreign Application Priority Data

May 9, 1990 [DE] Germany .......................... 40 14 845.9

[51] Int. Cl.$^6$ .............................. C12Q 1/68; C07H 17/00
[52] U.S. Cl. ............................... 435/6; 536/24.32; 935/8; 935/78
[58] Field of Search .............................. 435/6; 536/24.3, 536/24.32, 24.7; 935/8, 78

OTHER PUBLICATIONS

Sommer et al., "Minimal Requirements for PCR Primers", *Nucleic Acids Research*, vol. 17, No. 16, 1989, p. 6749.
A. Kornberg *DNA Synthesis*, pp. 16–17, W. H. Freeman and Co., San Francisco (1974).
S. W. Watson and M. Mandel J. Bacteriol. 107, 563–569 (1971).
J. Meinkoth and G. M. Wahl Methods in Enzymology 152, 91–94 (1987).
STN, Registry file, Gen Bank M15861 (9CI), sequence comparison of chicken to oligonucleotide of cl. 18.
ATCC Catalogue of Bacteria and Bacteriophages, 17th Edit., 1989, p. 152.
Nucleic Acid Hybridization: A practical approach, Hames et al., Editors, IRL Press, Oxford, pp. 73, 78, 79, 94, 96, 100, 102 and 123.

*Primary Examiner*—Margaret Parr
*Assistant Examiner*—Bradley L. Sisson
*Attorney, Agent, or Firm*—Sprung, Horn, Kramer & Woods

[57] ABSTRACT

For the detection and quantitative determination of nitrosomonas strains in wastewaters and soils, a gene probe is used which, by virtue of its complementary sequences, only hybridizes with parts of the genome of nitrosomonas strains from wastewater or soil samples and does not produce a positive hybridization signal with parts of the genome of other bacteria and the hybridized nucleic acid is quantitatively determined by means of a known label of the gene probe and thus provides a direct measure of the content of nitrosomonas strains in the wastewater or soil sample.

7 Claims, 3 Drawing Sheets

METHOD FOR THE DETECTION AND QUANTITATIVE DETERMINATION OF NITROSOMONAS STRAINS IN WASTEWATERS OR SOILS

This application is a continuation of application Ser. No. 692,745, filed Apr. 24, 1991, now abandoned.

BACKGROUND OF THE INVENTION

On account of its toxicity to fish, but above all on account of its contribution to the eutrophication of waters, ammonium is a substance which should be completely removed from wastewaters. Whereas there are numerous industrial processes for the removal of high concentrations of ammonium, the removal of ammonium in ppm concentrations can only be economically achieved by biological processes. This is done by two specialized groups of bacteria which derive their energy for the cell metabolism from the oxidation of ammonia to nitrite (ammonia oxidizers) and further to nitrate (nitrite oxidizers). The ammonia oxidizers use $CO_2$ as the sole carbon source while nitrite oxidizers use additional carbon sources. The nitrate formed can be reduced to nitrogen by a number of heterotrophic bacteria at low oxygen concentrations and can therefore be completely removed (see for example (1)).

However, disadvantages attending the microbial elimination of nitrogen lie in the low growth rates of the nitrificants. $CO_2$ is the sole carbon source so that cell growth is minimal. In addition, many organic compounds, such as isothiocyanates, amines, phenols and nitrogen-containing heterocycles inhibit the growth of ammonia-oxidizing bacteria. As a result, the biological elimination of nitrogen in industrial effluent treatment plants is seriously reduced.

Since nitrificants cannot be rapidly and quantitatively determined by microbiological culture methods, there have hitherto been no possibilities for recognizing changes in the quantity of nitrificants in wastewater populations and for achieving an optimal treatment capacity by corresponding control measures.

SUMMARY OF THE INVENTION

According to the invention, it has been possible to solve this problem through the construction of gene probes for these ammonia-oxidizing bacteria. Using these gene probes, nitrificants in complex biomasses, such as are present in wastewaters and soils, can be quantitatively determined from the concentration of nucleic acid. In the gene probe test, the gene probe and complementary target DNA from nitrificants are specifically duplexed (hybridized). The gene probe is produced either synthetically (up to 100 oligonucleotides) or biologically on the basis of the sequence described in the following and is provided with a label (radioactivity, dye, enzyme). Its addition to a sample material containing nitrificants, for example nucleic acid lysates from aeration sludge or soils, results in hybridization by the complementary sequences of gene probe and nitrificant DNA. This hybridization reaction can be carried out in solution or with nucleic acids fixed to carriers (nitrocellulose, nylon membranes, beads). The hybridized nucleic acid is quantitatively evaluated through the labeling of the gene probe and thus provides a direct measure of the nitrificant content of the biomass of the wastewater or soil.

The present invention also extends to gene probes isolated by the same method and to modified variants of the gene probes described in the invention which have the features and properties essential for carrying out the invention.

DESCRIPTION OF THE PREFERRED EMBODIMENTS

The main applications for the new gene probes are in the testing and monitoring of nitrificant concentrations in the biological elimination of nitrogen in waste water treatment plants.

The detection limit for the detection of nitrificants with the new gene probes is in the range of $10^5$ to $10^6$ bacteria.

The detection sensitivity can be distinctly improved by amplification methods, such as for example the PCR method (polymerase chain reaction). A detection limit of 10 to 100 bacteria can be achieved by amplification on the basis of the gene probe sequences described in the invention.

The invention is illustrated by the following Examples. Genetically engineered isolation of nitrosomonas gene probes The genomic nucleic acid from the strain Nitrosomonas europaea ATCC 19718 was isolated by a preparative lysozyme/SDS nucleic acid isolation method.

To construct gene probes, the genomic DNA was cleaved with the restriction enzyme BamHI into 1–15 kb large DNA fragments, linked to BamHI-linearized pBR322 plasmid vector by genetic engineering and transformed into competent E. coli cells AG1.

Ampicillin-resistant clones were isolated the next day and recombinant clones containing DNA of nitrosomonas were identified through the sensitivity to tetracycline of bacteria transformed with the plasmid vector. The cloning experiments were carried out by the genetic method described by Maniatis (2).

The plasmid DNA was isolated from the recombinant clones by an analytical nucleic acid isolation method and the size of the nitrosomonas DNA incorporated was determined by gel-electrophoretic separation. The exact size of clones containing incorporated nitrosomonas DNA in the 1–15 kb range was determined by cleavage of the plasmids with the restriction enzyme BamHI and by gel-electrophoretic separation of the linearized plasmids. Clones with the exact insert sizes of nitrosomonas DNA are listed in Table 1.

By reversed-phase hybridization, it was possible to determine which of the isolated nitrosomonas gene probes had the broadest detection spectrum for nitrosomonas. To this end, the individual gene probes were subjected to gel-electrophoretic separation in agarose gel and the gene probe DNA was subsequently transferred from the gel to a nitrocellulose filter and fixed. The genomic nitrosomonas DNA was suitably labeled ($P^{32}$-ATP, biotin, digoxigenin, enzyme) and used as a gene probe in Southern blotting with the gene probes fixed to a nitrocellulose filter.

A 6 kb gene probe SPN 323.13 was identified and produced a very strong hybridization signal in the Southern blotting hybridization test. This gene probe was analyzed for its nitrosomonas specificity by a dot blotting hybridization test. The experiments showed that the gene probe SPN 323.13 is specific for nitrosomonas and has the broadest detection spectrum for nitrosomonas of all the gene probes tested. This gene probe was used for the further development of shorter gene probes and chemically synthesized oligonucleotide gene probes.

Genetically engineered development of nitrosomonas gene probes

Figure 1:
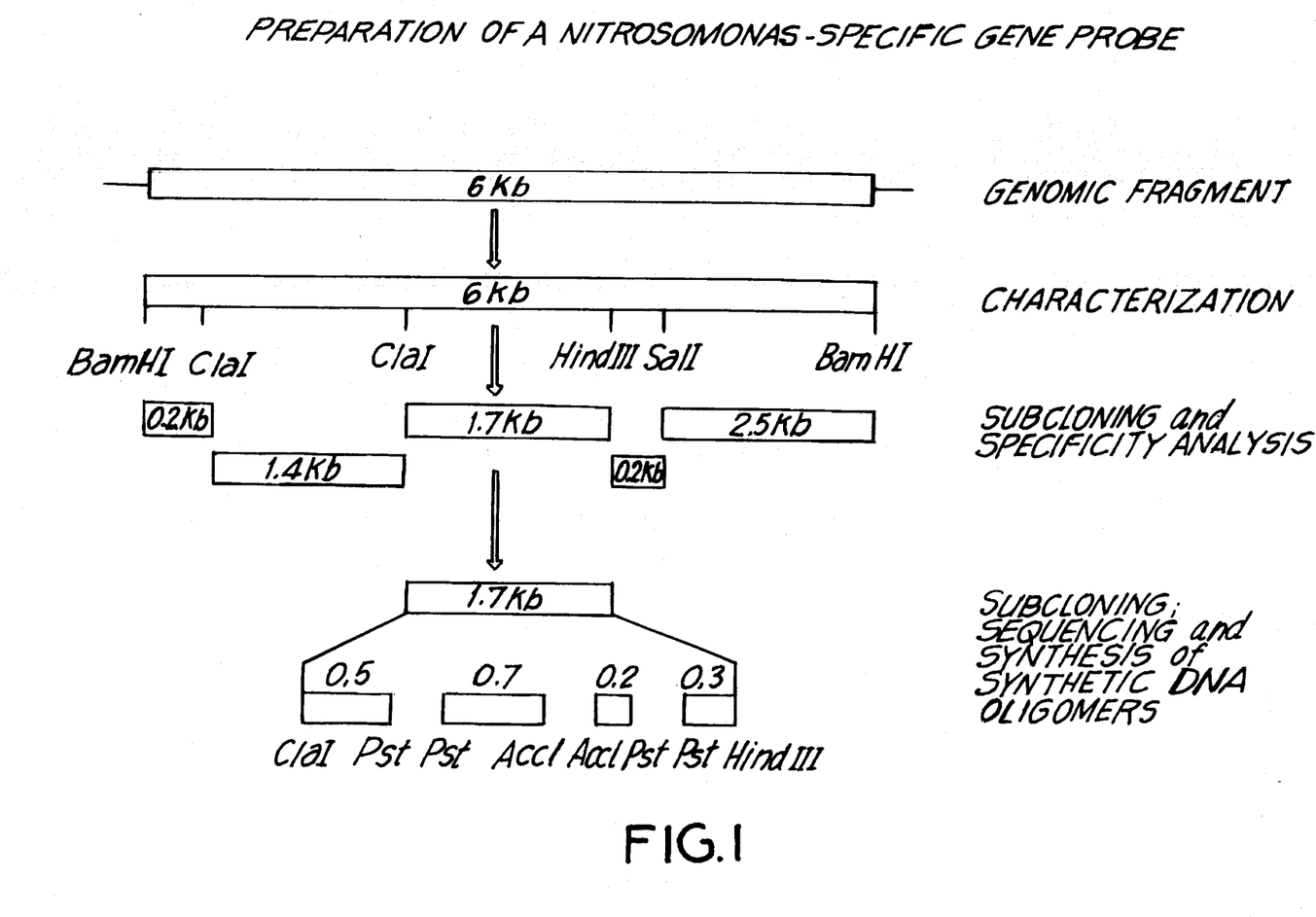
FIG. 1 is a schematic of the preparation of a nitrosomonas-specific gene probe.

Other shortened gene probes were constructed on the basis of the 6 kb gene probe SPN 323.13 (FIG. 1).

Figure 2:
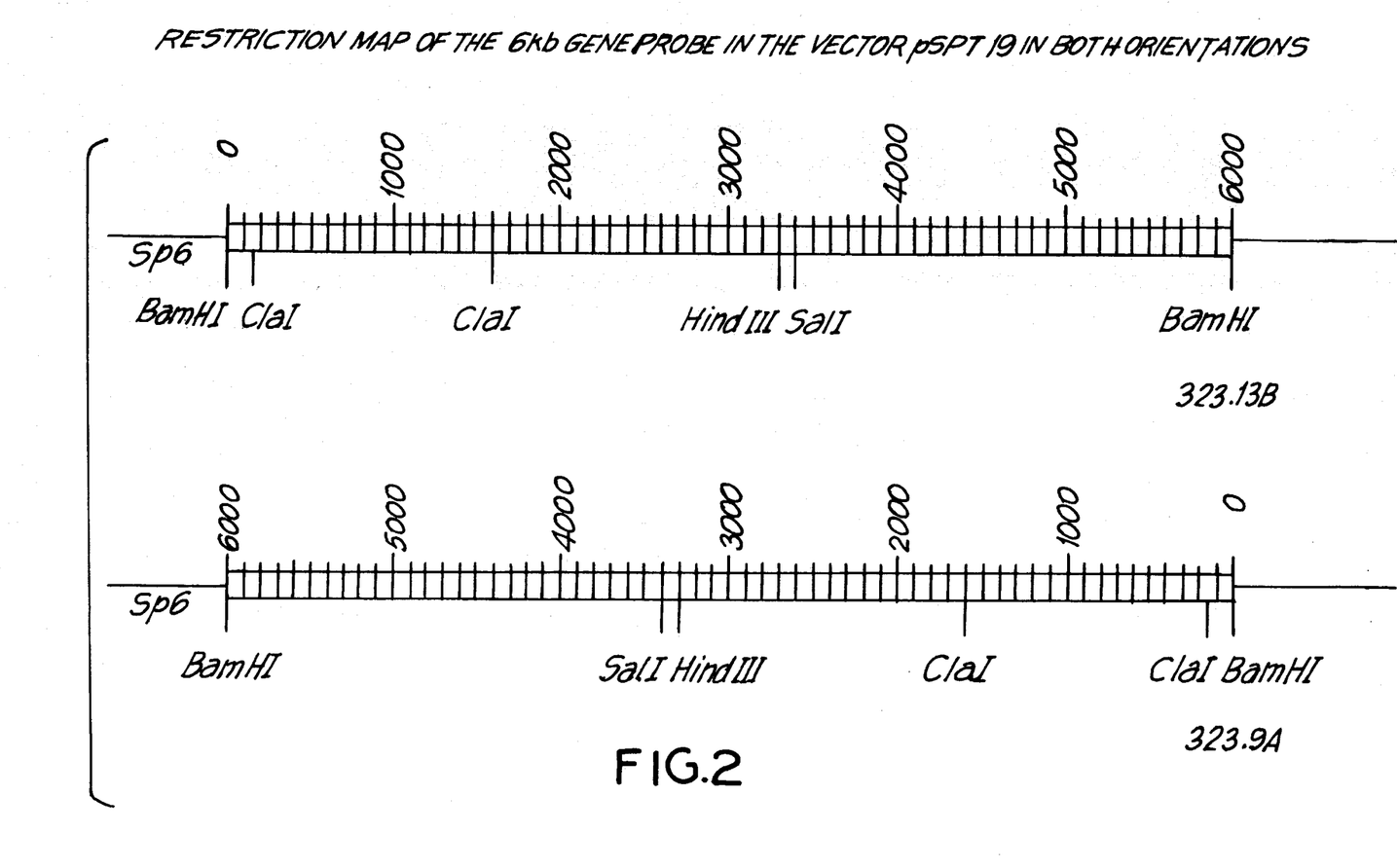
FIG. 2 is a restriction map of the 6 kb gene probe in the vector pSPT 19 in both orientations.

The gene probe was first molecular-biologically characterized by cleavage with various restriction enzymes. The linear restriction map of the gene probe is shown in both orientations in FIG. 2.

The 1.4 kb ClaI fragment, the 1.7 kb ClaI-HindIII fragment and the 2.5 kb SalI-BamHI fragment were subcloned into the vectors pBR 322 and pSK Bluescript (Stratagene).

Recombinant clones containing the individual gene fragments were isolated and molecular-biologically characterized. After cleavage with the corresponding restriction enzymes and gel-electrophoretic separation, the individual gene fragments were isolated by electroelution. These gene probes were then labeled with the usual labeling substances ($P^{32}$ ATP, biotin, digoxigenin, enzymes) and their specificity was determined in the gene probe test.

By virtue of its high specificity for nitrosomonas strains and its nevertheless very broad detection spectrum for nitrosomonas, the 1.7 kb gene probe SPN 366.1 was identified as particularly suitable for the detection of nitrosomonas.

Figure 3:
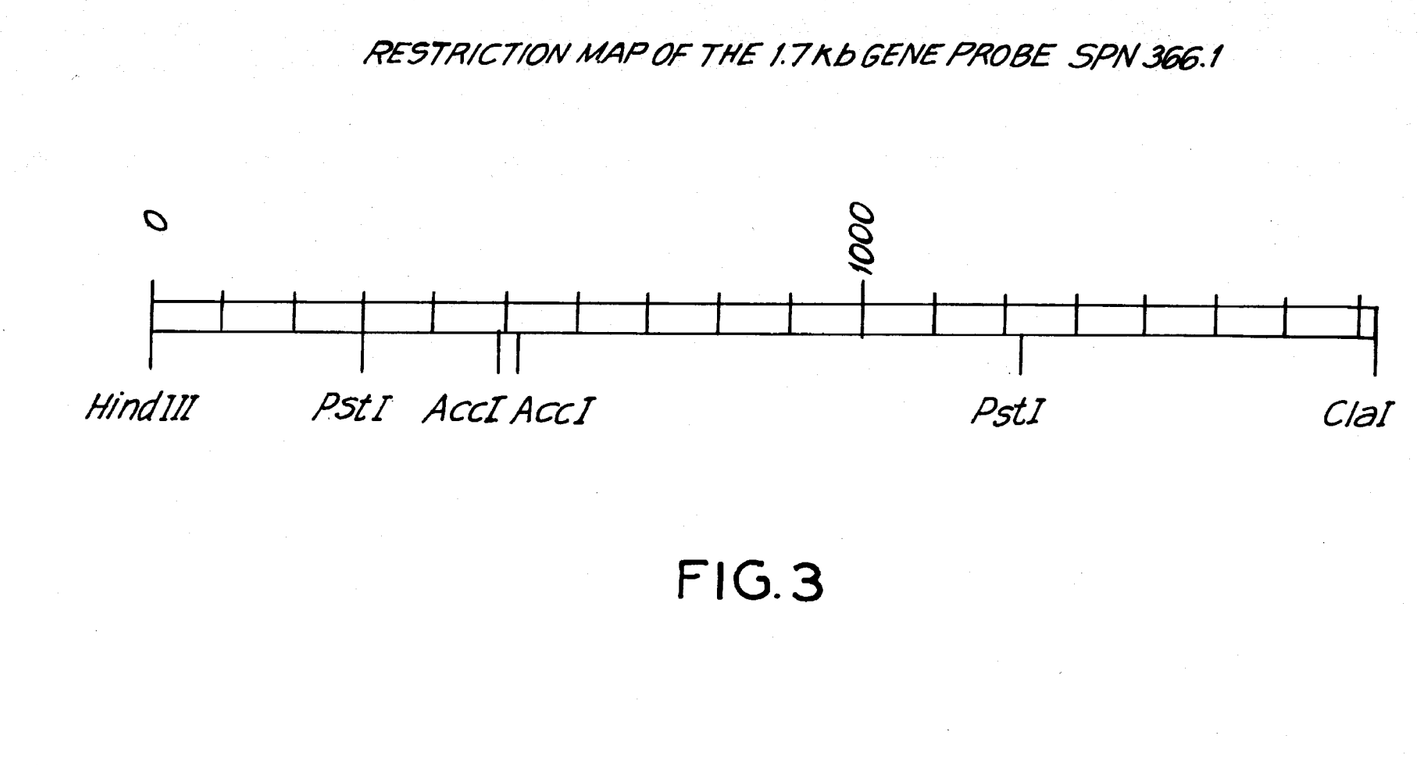
FIG. 3 is a restriction map of the 1.7 kb gene probe SPN 366.1.

For further optimization and synthesis of oligonucleotide gene probes, this gene probe was first molecular-biologically characterized by cleavage with restriction enzymes. The linear restriction map of the b 1.7kb gene probe SPN 366.1 is shown in FIG. 3.

To shorten the 1.7 kb gene probe SPN 366.1, the 0.2 kb, 0.3 kb, 0.5 kb and 0.7 kb gene fragments formed by cleavage with the restriction enzymes HindIII, AccI, PstI and ClaI and ClaI were subcloned into the vector pSK Bluescript (Stratagene).

The 0.2 kb, 0.3 kb, 0.5 kb and 0.7 kb gene probes were isolated from the corresponding constructs by electroelution after cleavage with restriction enzymes and gel-electrophoretic separation in agarose gel. The gene probes were labeled ($P^{32}$ ATP, biotin, digoxigenin-UTP, enzyme) by the random prime labeling method and subsequently tested for their specificity and sensitivity in the gene probe test. It was found that the gene probes SPN 391.7 (0.2 kb), SPN 397.1 (0.3 kb), SPN 391.3 (0.5 kb) and SPN 391.16 (0.7 kb) did not show any significant differences in regard to specificity and sensitivity of nitrosomonas detection and were all equally suitable for use as gene probes. The gene probe tests with the gene probes SPN 391.7, 397.1, 391.3 and 391.16 are shown by comparison with the 1.7 kb gene probe SPN 366.1 in Table 2.

Sequencing of the gene probe SPN 366.1

The 1.7 kb gene probe was sequenced on the basis of the gene probe SPN 366.1 (1.7 kb) and the 0.2 kb, 0.3 kb, 0.5 kb and 0.7 kb gene probes.

Sequencing was carried out by the Sanger dideoxy chain termination method (b 5). The nucleotide sequence of the 1.7 kb gene probe SPN 366.1 is shown in the attached sequence listing.

Chemical synthesis of oligonucleotide gene probes

Oligonucleotide gene probes were chemically synthesized on the basis of the existing sequence of the 1.7 kb gene probe SPN 366.1 by the amidite method of S. L. Beaucage and M. H. Caruthers (6).

By gene probe tests with various oligonucleotides from the region of the 1.7 kb gene sequence of the gene probe 366.1, it was found that 15 mer–100 mer oligonucleotide gene probes from any regions of the 1.7 kb gene probe can be used for the gene probe test.

The following oligonucleotide gene probes proved to be particularly suitable in the gene probe test: bases 1–53, bases 1315–1365, and bases 1610–1663 of SEQ ID No. 1.

Carrying out the gene probe test

To determine the specificity and sensitivity of the gene probes, a gene probe test was carried out with digoxigenin DUTP labeled gene probes using the Boehringer/Mannheim digoxigenin test kit.

Labeling the nitrosomonas gene probes

The gene probes were labeled with digoxigenin-dUTP by the random prime method of Feinberg and Vogelstein (3). Before the random prime labeling, the gene probes were cut out from the corresponding recombinant plasmids with restriction enzymes. The linearized gene probes were separated from the linearized plasmid vector by gel electrophoresis in 0.8% agarose gel. The gene probe DNA was cut out from the agarose gel and the gene probe was isolated from the agarose block by electroelution. The gene probe DNA was then further purified by extraction with phenol and precipitation with ethanol. Before labeling with digoxigenin-dUTP, the gene probe DNA was denatured by heating for 10 mins. in a water bath to 100° C. and rapid cooling on ice/NaCl. For labeling, 1 μg denatured gene probe DNA, 2 μl hexanucleotide mixture and 2 μl dNTP labeling mixture were combined, made up to 19 μl with sterile twice-distilled water and 1 μKlenow enzyme was added. Labeling with digoxigenin-dUTP was carried out for 60 mins. at 37° C. The reaction was then stopped by addition of 2 μl EDTA solution 0.2 mol/l pH 8 and the labeled DNA was precipitated with 2.5 μl LiCl 4 mol/l and 75 μl precooled ethanol (−20° C.). After 30 mins. at −70° C., the DNA precipitate was centrifuged off at 12,000 g and washed with cold ethanol, 70%, dried in vacuo and dissolved in 50 μl tris-HCl 10 mmol/l, EDTA 1 mmol/l pH 8.

Hybridization with nitrosomonas gene probes

For the hybridization experiments, the nitrosomonas-DNA-containing nucleic acid extracts from the biomass of wastewaters or soils were first denatured into the DNA single strands by heating for 10 minutes to 100° C. and rapid cooling on ice/NaCl. Nitrocellulose membranes were pretreated by swelling in water and 20×SSC (NaCl 3 mol/l, Na citrate 0.3 mol/l pH=7) and dried. Nylon membranes were used without any pretreatment. The denatured nucleic acid extracts were applied to the nitrocellulose or nylon membranes using a Schleicher & Schell Minifold II filtration unit and then fixed by baking in vacuo for 1 h at 80° C. or by UV crosslinking for 5 mins. using a UV transilluminator (nylon membrane).

The nylon/nitrocellulose filters were sealed in a plastic bag containing 20 ml hybridizing solution (5×SSC; blocking reagent 0.5%; N-lauroyl sarcosine, Na salt 0.1%; SDS 0.02%) and prehybridized for 1 hour at 68° C. The prehybridizing solution was then replaced by 2.5 ml hybridizing solution (same composition) containing freshly denatured gene probe DNA (100 ng). The hybridization batch was incubated for 2 hours at 68° C. The filters were then washed for 2×5 mins. at room temperature with 50 ml 2×SSC; SDS 0.1% and then again for 2×15 mins. at 68° C. with 0.1× SSC 0.1% SDS. The filters were directly used for the detection of the hybridized DNA or were stored in air-dried form for subsequent detection.

Detection of the hybridized nitrosomonas DNA

An immunological detection reaction was carried out for quantitative detection of the hybridized nitrosomonas DNA.

An antibody conjugate with coupled alk. phosphatase was used which binds to the hybridized digoxigenin-labeled DNA. The color reaction was started at an alkaline pH by addition of the colorless 5-bromo-4-chloro-3-indolyl phosphate and nitroblue tetrazolium. The blue precipitate formed was quantitatively evaluated after 2–12 hours with a Shimadzu CS430 densitometer. The following buffers were used for the detection reaction Buffer 1: Tris/HCl 100 mmol/l; NaCl 150 mmol/l pH 7.5

Buffer 2: 0.5% solution of blocking reagent in buffer 1

Buffer 3: Tris/HCl 100 mmol/l; NaCl 100 mmol/l, $MgCl_2$ 50 mmol/l pH 9.5

Buffer 4: Tris/HCl 10 mmol/l, EDTA 1 mmol/l pH 8 Dye solution (freshly prepared) 45 µl NBT and 35 µl X-phosphate were added to 10 ml buffer 3.

The nitrocellulose/nylon filters were washed for 1 minute in buffer 1, incubated for 30 minutes with 100 ml buffer 2 and rewashed with buffer 1. The antibody conjugate was diluted in a ratio of 1:5,000 in buffer 1 and the filters were incubated for 30 minutes with approx. 20 ml of the dilute antibody conjugate solution. Unbound antibody conjugate was removed by 2×15 mins. washing with 100 ml buffer 1 and the filters were subsequently equilibrated for 2 mins. with 20 ml buffer 3. The filters were then incubated with 20 ml dye solution in darkness in a sealed plastic bag. The color intensity of the individual slot blots was determined by densitometry by comparison with a co-applied nitrosomonas DNA standard.

Specificity of the gene probes

The specificity of the gene probes was analyzed by the described gene probe test. The nucleic acid was extracted from characterized gram-negative and gram-positive bacteria, including bacteria which degrade aromatic halogen compounds, aromatic nitro compounds, aromatic amino compounds, alkyl sulfonic acids and aryl sulfonic acids, and various nitrosomonas isolates and a dot blot hybridization test was carried out with the described gene probes to determine which bacterial lysates produced a positive hybridization signal (Table 2).

Through the experiments, it was found that the developed nitrosomonas gene probes hybridized specifically with all nitrosomonas lysates and did not produce any hybridization signals with other bacterial lysates.

Use of nitrosomonas gene probes for detecting and quantifying nitrosomonas in waters/wastewaters For detecting and quantifying nitrosomonas strains in waters/wastewaters, the total nucleic acid was first isolated from the centrifuged water/wastewater samples. 150 µl 10.5M EDTA and 150 µl twice-dist. $H_2O$ and 3 µl SDS, 20%, were added to 50 mg moist biomass which was then incubated in a water bath for 60 seconds at 100° C. and, immediately afterwards, was placed in an ice/salt bath for 1 minute. 600 µl Tris-saturated phenol was then added for the first extraction with phenol, followed after mixing by centrifugation for 5 minutes at 5,000 G. The extraction with phenol was repeated with the upper aqueous DNA phase. Small amounts of phenol were removed by subsequent extraction with ether. The ether phase was removed, the DNA was precipitated with isopropanol and was then centrifuged off at 5,000 G in a tabletop centrifuge. The DNA pellet was washed with 70% ethanol. The DNA pellet was then taken up in 220 µl TE buffer and, as described with reference to the gene probe test procedure, was fixed to nitrocellulose or nylon membranes and then hybridized with the described gene probes.

For quantifying, nitrosomonas DNA standard was applied in concentrations of 250 ng to 3.5 ng corresponding to cell numbers of $2.5 \times 10^6$ to $3.5 \times 10^4$ nitrosomonas cells. The positive hybridization reaction was evaluated on the basis of the color intensity of the 5-bromo-4-chloro-3-indolyl nitroblue tetrazolium complex in a Shimadzu CS930 densitometer. The concentration of the nitrosomonas-specific DNA respectively the nitrosomonas cell titer in the sample material was determined by comparison with the slot blots of the nitrosomonas DNA standard. The detection limit of the described detection method was $10^5$–$10^6$ nitrosomonas bacteria.

Use of nitrosomonas gene probes for detecting and quantifying nitrosomonas strains in soils For detecting and quantifying nitrosomonas bacteria in soils, the nucleic acid of bacteria present in the soil was isolated by the method of Torsvik and Marmur (4).

100 ml TE buffer (Tris/HCl 10 mmol/l, EDTA 1 mmol/l pH 8) were added to 10 g soil, the sample was thoroughly mixed and the soil was subsequently separated from the bacterial extract by filtration. The bacteria were separated from the filtrate by centrifugation at 5,000 g. The bacterial fraction was washed once with 100 ml 0.1M $Na_4P_2O_7$ (pH 7) and once with 100 ml 0.15M NaCl, 10 mM EDTA (Saline EDTA) and, after centrifugation at 5,000 g, was resuspended in 25 ml Saline EDTA. By addition of 1 mg/ml lysozyme and subsequent incubation for 30 minutes at 37° C., the bacteria were lysed with sodium dodecyl sulfate (SDS) in a final concentration of 1%. In order to remove most of the humic substances still present in the soil, further purification can be achieved by ion exchange chromatography and hydroxylapatite chromatography or pronase, RNase treatment and extraction with phenol.

As described with reference to the gene probe test procedure, the DNA was fixed to nitrocellulose or nylon membranes and the hybridization reaction was carried out with the Boehringer/Mannheim digoxigenin test kit. The nitrosomonas-specific DNA concentration or cell titer was quantitatively evaluated from the color intensity of the 5-bromo-4-chloro-3-indolyl nitroblue tetrazolium complex of the slot blots.

TABLE 1

Molecular characterization of nitrosomonas clones

| Clone code | Vector  | Insert [KB] | Strain       |
|------------|---------|-------------|--------------|
| 256/15     | pBR 322 | 2.7         | Nitrosomonas |
| 256/32     | pBR 322 | 5.8         | Nitrosomonas |
| 256/36     | pBR 322 | 2.3         | Nitrosomonas |
| 256/39     | pBR 322 | 1.3         | Nitrosomonas |
| 258/21     | pBR 322 | 3.9         | Nitrosomonas |
| 258/22     | pBR 322 | 5.9         | Nitrosomonas |
| 258/23     | pBR 322 | 3.3         | Nitrosomonas |
| 258/27     | pBR 322 | 21.6        | Nitrosomonas |
| 258/29     | pBR 322 | 6.0         | Nitrosomonas |
| 258/33     | pBR 322 | 3.4         | Nitrosomonas |
| 258/34     | pBR 322 | 7.1         | Nitrosomonas |
| 258/35     | pBR 322 | 7.5         | Nitrosomonas |
| 323/9A     | pSPT 19 | 6.0         | Nitrosomonas |
| 323/13B    | pSPT 19 | 6.0         | Nitrosomonas |
| 322/9A     | pSK     | 6.0         | Nitrosomonas |
| 322/10B    | pSK     | 6.0         | Nitrosomonas |

Nitrosomonas DNA clones as BamHI fragments in the *E. coli* vector pBR 322 into *E. coli* 5K or AG1. The genomic DNA was isolated from the strain Nitrosomonas europaea 9718 and cloned. The 6 kb gene probe from 258/29 was recloned in both orientations into the vectors pSPT19 and pSK Bluescript.

TABLE 2

Specificity of the nitrosomonas gene probe

| Strain | Degradation of | Hybridization with | | | | |
|---|---|---|---|---|---|---|
| | | 0.2kb | 0.3kb | 0.5kb | 0.7kb | 1.7kb |
| Nm. europaea | Ammonia | + | + | + | + | ++ |
| Nm. spec. 41-3/BE | Ammonia | ++ | ++ | ++ | ++ | +++ |
| Nm. spec. LA33 | Ammonia | ++ | ++ | ++ | ++ | +++ |
| Nm. spec. 41-3/GB | Ammonia | + | + | + | + | ++ |
| Nm. spec. 41-3/RW | Ammonia | + | + | + | + | ++ |
| Nm. spec. A 83 | Ammonia | + | + | + | + | ++ |
| Nm. spec. A 13 | Ammonia | + | + | + | + | ++ |
| Nl. multiformis | Ammonia | – | – | – | – | – |
| Nb. agilis | Nitrite | – | – | – | – | – |
| Th. pantotropha | Sulfur | – | – | – | – | – |
| Tb. novellus | Sulfur | – | – | – | – | – |
| Tb. perometab | Sulfur | – | – | – | – | – |
| Tb. acidophilus | Sulfur | – | – | – | – | – |
| Alc. faccalis | | – | – | – | – | – |
| Str. facalis | | – | – | – | – | – |
| Staph. capitis | | – | – | – | – | – |
| Kl. planticola | | – | – | – | – | – |
| Microb. lacticum | | – | – | – | – | – |
| E. coli 5k | | – | – | – | – | – |
| P. spec 61-Tol4 | Toluene | – | – | – | – | – |
| P. syringae 50-16 | Sulfonic acid | – | – | – | – | – |
| P. putida 82-1 | Nitrobenz. | – | – | – | – | – |
| Ps. putida NCIB 12042 | Naphthalene | – | – | – | – | – |
| Br. spec. 233 | Polycycles | – | – | – | – | – |
| Alcal. spec. 67-1.4R4 | Benzene | – | – | – | – | – |
| Ps. spec. 67-D3/2 | Benzene | – | – | – | – | – |
| M. spec. 1.2/2 | Dichlorob. | – | – | – | – | – |

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 1722 bp
        ( B ) TYPE: Nucleotide
        ( C ) STRANDEDNESS: Double
        ( D ) TOPOLOGY: Linear     ( i i ) MOLECULE TYPE: Genomic DNA     ( x i ) SEQUENCE DESCRIPTION: SEQ ID NO:1:

```
TTAGAAGTA ATG AGC CCA TGG CTA TTT GCC GCG CAT AAA CAT    42
          Met Ser Pro Trp Leu Phe Ala Ala His Lys His

TTT ATC CAG TTC AGC CAG GCT GAT TTC AAA CCA GGT AGG       81
Phe Ile Gln Phe Ser Gln Ala Asp Phe Lys Pro Gly Arg

TCG GCC GTG ATT GCA TTG ATC CGA GCG CTC GGT TAC TTC       120
Ser Ala Val Ile Ala Leu Ile Arg Ala Leu Gly Tyr Phe

CAT TTT GCG CAG AGT TCA TTC ATT TCA ATC AGC GTT AAT       159
His Phe Ala Gln Ser Ser Phe Ile Ser Ile Ser Val Asn

TGC CGG TTA GCG CGA ACG GCA CCG TGA CAG GCC ATG GTG       198
Cys Arg Leu Ala Arg Thr Ala Pro     Gln Ala Met Val

GCC AGT AAT TCA TTA CDA CGG GCG GCA AGC AGT TGA GCG       237
Ala Ser Asn Ser Leu Xaa Arg Ala Ala Ser Ser     Ala

GGA TCG CCA TTC CTG ATT TCA TCC AGC AGA GCA CGT ACC       276
Gly Ser Pro Phe Leu Ile Ser Ser Ser Arg Ala Arg Thr

AGT TTC GCA TCA GCA TGC TGC AGT GTG GCG GGG ACT GTG       315
Ser Phe Ala Ser Ala Cys Cys Ser Val Ala Gly Thr Val

CGT ATA ACA AGT GTG GTA GCG GAC AGC GTG CTC ACT TCA       354
Arg Ile Thr Ser Val Val Ala Asp Ser Val Leu Thr Ser

AAA CAC AGT TGC TGC AAA AGC GCC TGA TTT TCC TCC ACT       393
Lys His Ser Cys Cys Lys Ser Ala     Phe Ser Ser Thr

GTC GCG ATG TCG AGG CTA TCT GCG TGA AAT GTA ACC GGT       432
```

|     |     |     |     |     |     |     |     |     |     |     |     |     |      |
|-----|-----|-----|-----|-----|-----|-----|-----|-----|-----|-----|-----|-----|------|
| Val | Ala | Met | Ser | Arg | Leu | Ser | Ala |     | Asn | Val | Thr | Gly |      |
| ATC | AGC | AAT | CGG | TTG | TGC | GGA | TAA | TAC | TTG | TTG | ATC | CAG | 471  |
| Ile | Ser | Asn | Arg | Leu | Cys | Gly |     | Tyr | Leu | Leu | Ile | Gln |      |
| TTG | TGT | CTT | CAA | CTG | CTC | GTA | GAC | AAT | GCG | TTC | GTG | CGC | 510  |
| Leu | Cys | Leu | Gln | Leu | Leu | Val | Asp | Asn | Ala | Phe | Val | Arg |      |
| GGC | GTG | CAT | GTC | TAC | AAT | CAC | CAA | TCC | TTT | TTG | GTT | TTG | 549  |
| Gly | Val | His | Val | Tyr | Asn | His | Gln | Ser | Phe | Leu | Val | Leu |      |
| CGC | CAG | GAT | ATA | GAT | GCC | GCG | AAG | TGC | CCC | AAC | GCA | AAG | 588  |
| Arg | Gln | Asp | Ile | Asp | Ala | Ala | Lys | Cys | Pro | Asn | Ala | Lys |      |
| CCC | AGC | GGG | GGC | ATA | GCC | GAA | TTT | TCA | TCG | CTT | TCT | CCT | 627  |
| Pro | Ser | Gly | Gly | Ile | Ala | Glu | Phe | Ser | Ser | Leu | Ser | Pro |      |
| TCC | CCG | GTT | TGT | CGA | GGT | TGA | TTT | TGT | ATG | GCA | GTG | GCG | 666  |
| Ser | Pro | Val | Cys | Arg | Gly |     | Phe | Cys | Met | Ala | Val | Ala |      |
| CCG | GAT | TCT | CCG | CCG | GAT | AGA | ACC | TGA | TAA | AAG | TTA | AAA | 705  |
| Pro | Asp | Ser | Pro | Pro | Asp | Arg | Thr |     |     | Lys | Leu | Lys |      |
| GGG | TGC | GCC | ACC | CTT | TCT | GAT | GAC | AGC | CGT | GCT | TGC | CTG | 744  |
| Gly | Cys | Ala | Thr | Leu | Ser | Asp | Asp | Ser | Arg | Ala | Cys | Leu |      |
| GGG | TAG | TTC | AAC | GTC | CAC | AGC | CGG | TGT | AAA | ACC | GGT | GCG | 783  |
| Gly |     | Phe | Asn | Val | His | Ser | Arg | Cys | Lys | Thr | Gly | Ala |      |
| CGT | TGG | ATC | AAC | AGA | TGC | ATC | CTG | CGT | ACC | TGG | CCA | CAC | 822  |
| Arg | Trp | Ile | Asn | Arg | Cys | Ile | Leu | Arg | Thr | Trp | Pro | His |      |
| GGC | CCC | AAC | AGG | AGA | GGA | GGA | TGC | TAC | AGC | CGA | GCG | GGG | 861  |
| Gly | Pro | Asn | Arg | Arg | Gly | Gly | Cys | Tyr | Ser | Arg | Ala | Gly |      |
| TAG | AGC | CAG | CGC | CTT | GTG | ACG | CCG | TGG | TAA | ATA | AAT | TGG | 900  |
|     | Ser | Gln | Arg | Leu | Val | Thr | Pro | Trp |     | Ile | Asn | Trp |      |
| TGG | ATG | GCC | CGC | TTC | GGC | GAA | AGC | GAC | TAC | GTT | TCG | TCG | 939  |
| Trp | Met | Ala | Arg | Phe | Gly | Glu | Ser | Asp | Tyr | Val | Ser | Ser |      |
| ATG | TAC | GTT | GAC | ATC | CAC | CTG | TTC | AGG | ATC | GAT | CGC | CAG | 978  |
| Met | Tyr | Val | Asp | Ile | His | Leu | Phe | Arg | Ile | Asp | Arg | Gln |      |
| ATA | CAG | CAC | GAA | AGC | GGC | ATG | ACG | ATC | AAG | GTG | CAG | CAC | 1017 |
| Ile | Gln | His | Glu | Ser | Gly | Met | Thr | Ile | Lys | Val | Gln | His |      |
| ATC | ACG | ATA | GCT | TCG | CGC | AGG | GCA | TGG | GTA | ATC | AGC | TTG | 1056 |
| Ile | Thr | Ile | Ala | Ser | Arg | Arg | Ala | Trp | Val | Ile | Ser | Leu |      |
| TCG | CGG | ATG | AAG | CGT | CCG | TTA | ACA | AAA | AAA | TAC | TGC | ATG | 1095 |
| Ser | Arg | Met | Lys | Arg | Pro | Leu | Thr | Lys | Lys | Tyr | Cys | Met |      |
| TCG | CGG | GTG | GCG | CGT | GAA | TAC | GCG | GGC | AAT | GCC | AGC | ATC | 1134 |
| Ser | Arg | Val | Ala | Arg | Glu | Tyr | Ala | Gly | Asn | Ala | Ser | Ile |      |
| CCC | TGC | AAA | CCG | ATG | CCG | GCG | GAT | TGT | TCG | TCC | ATC | CAG | 1173 |
| Pro | Cys | Lys | Pro | Met | Pro | Ala | Asp | Cys | Ser | Ser | Ile | Gln |      |
| GTA | GCC | GNT | CCG | GCA | AAT | TCC | TCG | CCA | AGT | ACG | GCT | CCG | 1212 |
| Val | Ala | Xaa | Pro | Ala | Asn | Ser | Ser | Pro | Ser | Thr | Ala | Pro |      |
| ATA | CGC | TCT | GCA | GCC | TCT | GCT | GCC | TGC | CAG | TGC | TGC | GCA | 1251 |
| Ile | Arg | Ser | Ala | Ala | Ser | Ala | Ala | Cys | Gln | Cys | Cys | Ala |      |
| GGT | TTC | CAT | TGT | GCC | GCA | GCG | TAA | AGG | TAA | TAT | CAG | CGT | 1290 |
| Gly | Phe | His | Cys | Ala | Ala | Ala |     | Arg |     | Tyr | Gln | Arg |      |
| GGG | AAA | GTG | CCA | TCC | GCC | GAA | AAA | CTT | CTT | CGC | AGT | GGG | 1329 |
| Gly | Lys | Val | Pro | Ser | Ala | Glu | Lys | Leu | Leu | Arg | Ser | Gly |      |
| CAA | ACT | CTG | TAG | CTT | CTG | TTT | TAA | GAA | ATT | TGC | GGC | GGG | 1368 |
| Gln | Thr | Leu |     | Leu | Leu | Phe |     | Glu | Ile | Cys | Gly | Gly |      |
| CAG | GCA | GGT | TGA | AAA | ACA | GAT | CCC | GGA | CTT | CAA | CCG | TAG | 1407 |
| Gln | Ala | Gly |     | Lys | Thr | Asp | Pro | Gly | Leu | Gln | Pro |     |      |
| TGC | CCG | CCA | TGT | GGG | ATG | AAG | GCT | CCG | GCG | ACA | TTA | ACG | 1446 |
| Cys | Pro | Pro | Cys | Gly | Met | Lys | Ala | Pro | Ala | Thr | Leu | Thr |      |

| | | | | | | | | | | | | | |
|---|---|---|---|---|---|---|---|---|---|---|---|---|---|
| TGT | CCC | CTC | ACT | GCG | GAT | TTC | CCA | GGC | ATG | TTT | GCC | AGC | 1485 |
| Cys | Pro | Leu | Thr | Ala | Asp | Phe | Pro | Gly | Met | Phe | Ala | Ser | |
| GGG | TTG | ATG | ACT | GAT | GAG | CGA | CAA | ATA | CGA | AAC | TGA | CGC | 1524 |
| Gly | Leu | Met | Thr | Asp | Glu | Arg | Gln | Ile | Arg | Asn | | Arg | |
| GAT | ACT | GGC | CAG | CCC | TTC | CCC | CCG | GAA | TCC | CAG | GCT | GGT | 1563 |
| Asp | Thr | Gly | Gln | Pro | Phe | Pro | Pro | Glu | Ser | Gln | Ala | Gly | |
| GAT | GCT | GTG | CAA | ATC | CTC | CTG | GCT | GGC | AAT | TTT | GCT | GGT | 1602 |
| Asp | Ala | Val | Gln | Ile | Leu | Leu | Ala | Gly | Asn | Phe | Ala | Gly | |
| TGC | GTG | ACG | TGT | AAG | TGC | AAG | CGG | CAG | TTC | TTC | TGC | GGG | 1641 |
| Cys | Val | Thr | Cys | Lys | Cys | Lys | Arg | Gln | Phe | Phe | Cys | Gly | |
| AAT | GCC | GCT | GCC | GTT | ATC | GGT | CAC | ACG | GAT | CAG | TTT | CAA | 1680 |
| Asn | Ala | Ala | Ala | Val | Ile | Gly | His | Thr | Asp | Gln | Phe | Gln | |
| TCC | ACC | CTG | TGC | GAT | ATT | GAC | CGT | AAT | CTC | AGT | CGC | ACC | 1719 |
| Ser | Thr | Leu | Cys | Asp | Ile | Asp | Arg | Asn | Leu | Ser | Arg | Thr | |
| GGC | | | | | | | | | | | | | 1722 |
| Gly | | | | | | | | | | | | | |

Literature

1. "Autrophic Nitrification in Bacteria", J. I. Prosser, Adv. in Microbiol Physiol, 30, 125–177 (1989)
2. Molecular Cloning A Laboratory Manual, J. Sambrook, E. F. Fritsch, T. Maniatis, Cold Spring Harbor Laboratory Press (1989)
3. "A Technique for Radiolabeling DNA Restriction Endonuclease Fragments to High Specific Activity" A. P. Feinberg and B. Vogelstein, Anal Biochem 132, 6 (1983)
4. "Isolation of Bacterial DNA from Soil," V. L. Torsvik, Soil Biol. Biochem. 12, 10–21 (1980)
5. "DNA Sequencing with Chain-Terminating Inhibitors" F. Sanger, S. Nichlen, A. R. Coulson, P .N .A. S. 7x, 5463 (1977)
6. "Deoxynucleoside Phosphoramidites; A New Class of Key Intermediates for Deoxypolynucleotide Synthesis", C. L. Beaucage and M. H. Caruthers, Tetrahedron Letters 22, 1859–1862 (1981)

We claim:

1. A DNA probe consisting of a labeled continuous fragment of SEQ ID No. 1, said fragment being selected from the group consisting of:
   (i) a 0.2 kb PstI/AccI digestion fragment of SEQ ID No. 1;
   (ii) a 0.3 kb PstI/HindIII digestion fragment of SEQ ID No. 1;
   (iii) a 0.5 kb ClaI/PstI digestion fragment of SEQ ID No. 1;
   (iv) a 0.7 kb PstI/AccI digestion fragment of SEQ ID No. 1; and
   (v) a continuous fragment of SEQ ID No. 1 which is a 15 mer to 100 mer and which specifically hybridizes to Nitrosomonas strains from wastewaters or soil samples, but not to the genome of other bacteria.

2. A DNA probe according to claim 1 consisting of labeled and nucleotides 1–53 in the nucleotide sequence of SEQ ID No. 1.

3. A DNA probe according to claim 1 of labeled nucleotides 1315–1365 in the nucleotide sequence of SEQ ID No. 1.

4. A DNA probe according to claim 1 of labeled and nucleotides 1610–1663 in the nucleotide sequence of SEQ ID No. 1.

5. A DNA probe according to claim 1 consisting of a labeled 15 mer to 100 mer nucleotide continuous fragment from the nucleotide sequence of SEQ ID No. 1.

6. A DNA probe consisting of a labeled 1.7 kb ClaI-HindIII gene fragment which has the nucleotide sequence of SEQ ID No. 1.

7. A method for the detection and/or quantitation of Nitrosomonas strains in wastewaters and soils, said method comprising
   (a) providing a detectably labeled probe according to claims 2, 3, 4 or 1;
   (b) isolating total DNA from a wastewater or soil sample;
   (c) exposing said isolated total DNA to said detectably labeled probe under conditions under which said probe hybridizes to only the nucleic acid of Nitrosomonas strains;
   (d) detecting the hybridized probe; and
   (e) correlating the presence and intensity of said probe that is hybridized to known quantities of Nitrosomonas strains with the amount of signal generated from said probe hybridized to the DNA isolated from the sample to provide (i) an indication of the presence of Nitrosomonas strains in said wastewater or soil sample and/or (ii) a direct measure of the quantity of Nitrosomonas strains in said wastewater or soil sample.

* * * * *

UNITED STATES PATENT AND TRADEMARK OFFICE
CERTIFICATE OF CORRECTION

PATENT NO. : 5,462,855
DATED : October 31, 1995
INVENTOR(S) : Springer, et al.

It is certified that error appears in the above-indentified patent and that said Letters Patent is hereby corrected as shown below:

Col. 11, line 48    Delete " Psti/AccI " and substitute -- PstI/AccI --

Col. 12, line 26    Delete " and "

Col. 12, line 28    After " claim 1 " insert -- consisting --

Col. 12, line 31    After " claim 1 " insert -- consisting --, after " labeled " delete " and "

Col. 12, line 44    After " 4 " insert -- ,6, 5 --

Signed and Sealed this

Sixteenth Day of April, 1996

Attest:

BRUCE LEHMAN

Attesting Officer

Commissioner of Patents and Trademarks